United States Patent [19]
Mine

[11] Patent Number: 5,628,322
[45] Date of Patent: May 13, 1997

[54] METHOD OF ULTRASOUND IMAGING AND DIAGNOSTIC ULTRASOUND SYSTEM

[75] Inventor: Yoshitaka Mine, Nishinasuno-Machi, Japan

[73] Assignee: Kabushiki Kaisha Toshiba, Kawasaki, Japan

[21] Appl. No.: 645,751

[22] Filed: May 14, 1996

[30] Foreign Application Priority Data

May 15, 1995 [JP] Japan .................................. 7-116120

[51] Int. Cl.$^6$ ...................................................... A61B 8/00
[52] U.S. Cl. ........................ 128/661.08; 128/662.02; 128/660.05
[58] Field of Search ........................ 128/660.02, 660.05, 128/660.06, 661.07, 661.08, 661.09, 661.1, 662.01, 662.02; 73/861.25

[56] References Cited

U.S. PATENT DOCUMENTS

| | | | |
|---|---|---|---|
| 5,197,477 | 3/1993 | Peterson et al. | 128/661.08 |
| 5,271,404 | 12/1993 | Corl et al. | 128/661.09 |

FOREIGN PATENT DOCUMENTS

| | | | |
|---|---|---|---|
| 0357164 | 3/1990 | European Pat. Off. | |
| 3829999 | 3/1990 | Germany | |
| 4501518 | 3/1992 | Japan | |
| 584246 | 4/1993 | Japan | |
| 6114059 | 4/1994 | Japan | |

OTHER PUBLICATIONS

J. Acoust. Soc. Am., vol. 91, No.4, p. 2324, May 12, 1992, S. Smith, et al., "A Dual Frequency Ultrasonic Probe for Medical Application".

Ultrasonic Imaging, vol. 14, pp. 134–158, 1992, B. Schrope, et al., "Simulated Capillary Blood Flow Measurement Using a Nonlinear Ultrasonic Contrast Agent".

Radiology, vol. 182, p. 142, 1992, P.N. Burns, et al., "Harmonic Imaging: New Imaging and Doppler Method for Contrast-Enhanced Ultrasound".

Primary Examiner—George Manuel
Attorney, Agent, or Firm—Oblon, Spivak, McClelland, Maier & Neustadt, P.C.

[57] ABSTRACT

Using a Doppler technique, contrast echo imaging is carried out in order to properly measure the velocity of a contrast medium injected into a patient body by intravenous injection. A diagnostic ultrasound system includes: a unit for extracting a Doppler shift of a nonlinear echo component from a received echo, the nonlinear echo component being attributable to reflection of an ultrasound beam from the ultrasound contrast medium injected into blood. A unit converts a Doppler shift $f_d$ into a velocity component v according to the following conversion expression:

$$v = V\cos\theta = Cf_d/(2f_{set}+f_d)$$

where C denotes a sound velocity, V denotes a moving velocity of a blood flow in a patient body, v denotes a component of a moving velocity V in a direction of an ultrasound beam, θ denotes an angle of an ultrasound beam with respect to a moving direction of an object, $f_{set}$ denotes a set frequency used for velocity conversion, and $f_d$ denotes a Doppler shift. Further, a unit displays velocity information concerning the blood flow on the basis of the velocity component v. Preferably, the set frequency $f_{set}$ is the frequency of a reference signal employed in the system, which is set outside a frequency band of the ultrasound beam being transmitted.

24 Claims, 8 Drawing Sheets

0.59m/s

−0.59m/s 0.03

1

METHOD OF ULTRASOUND IMAGING AND DIAGNOSTIC ULTRASOUND SYSTEM

BACKGROUND OF THE INVENTION

1. Field of the Invention

The present invention relates to an ultrasound imaging method and a diagnostic ultrasound system capable of producing a contrast echo image by utilizing the nature of echoes that are enhanced due to the strong scattering characteristic of an ultrasound contrast medium, which is injected into a patient body, relative to ultrasonic waves, and of measuring the velocity of the contrast medium using a Doppler technique.

2. Description of the Related Art

In recent years, contrast echo techniques using an ultrasound contrast medium have drawn attention in the field of analysis of myocardial images.

A myocardial contrast echo technique accompanied by intra-arterial injection of an ultrasound contrast medium through the artery has been studied as one of the contrast echo techniques. The technique is used to produce a perfusion image and thus assess a region that is perfused by way of a myocardial blood flow. The myocardial contrast echo technique is such that an ultrasound contrast medium (for example, 5%-diluted human albumin having a foam produced manually or by means of a sonicator) is injected via a catheter indwelled in the aorta. A region perfused by way of a myocardial blood flow is displayed as an enhancement area in a B-mode image owing to the contrast medium. Likewise, a contrast echo technique accompanied by intra-arterial injection has been studied even for examination of an abdominal region in an effort to assess a tumor perfused by the hepatic artery. A diagnostic ultrasound system for general studies and/or a workstation are used as a diagnostic system in which these contrast echo techniques are implemented. Thus, enhancement in a B-mode image may be evaluated through a visual check, or a change in luminance level may be evaluated quantitatively after image data stored in a memory is properly processed within the workstation.

Moreover, recently, development of ultrasound contrast media themselves is in earnest. Ultrasound contrast media enabling assessment of the left heart through intravenous injection have been developed. An ultrasound contrast echo technique using this kind of contrast medium has been put to trial.

The ultrasound contrast media include, for example, "a microbubble which is made by infusing air into an albumin membrane produced when the 5%-diluted human albumin is processed by ultrasonic waves and in which an average diameter of a particle is approximately 4 micrometers" (product name: Albunex injection 5 ml) which is imported and sold by Shionogi Co., and Ltd.

Among the aforesaid known contrast echo techniques, a contrast echo technique accompanied by intra-arterial injection makes it necessary to indwell a catheter in the aorta and is therefore limited to hospitals having a relatively large facility (operating room) enabling the indwelling. Moreover, a large load must be incurred by a patient because this diagnostic procedure is invasive. For these reasons, the scanning technique will presumably not penetrate general clinical sites.

Bubbles of a contrast medium to be injected intra-arterially are relatively large. The bubbles are likely to become stagnant in the cardiac muscle or a capillary bed region. An enhancement may persist for several minutes. Therefore, even when Doppler measurement is performed on these vascular regions, the moving velocity of bubbles does not accurately reflect a blood flow velocity.

By contrast, a contrast echo technique accompanied by intravenous injection is the least invasive and imposes only a small load on a patient. However, a contrast medium reaches the cardiac muscle or any other intended region through the lung. Compared with the contrast echo technique accompanied by intra-arterial injection, the concentration of a contrast medium is low and the degree of enhancement is low. In a region prone to the influence of echoes emanating from surrounding tissues; such as, the cardiac muscle or the peripheral region of the abdomen, it is very hard to observe enhancement attained by a contrast medium. It is the current situation that this technique cannot be employed in assessment of a region perfused by way of a myocardial blood flow using a perfusion image or detection of a blood flow in the parenchyma of the liver.

Moreover, for producing color Doppler images, the influence of motion artifacts stemming from the motions of surrounding tissues or the motions of vascular walls, which are caused by respiration or the like, is so large in examination of, especially, the abdomen, that a produced image does not serve as a color Doppler image.

SUMMARY OF THE INVENTION

An object of the present invention is to attempt to break through the current situation of the known contrast echo techniques using ultrasound contrast media and to provide a diagnostic ultrasound system capable of more accurately measuring the velocity of a contrast medium using a Doppler technique by performing contrast echo imaging accompanied by intravenous injection even in case a region is prone to the influence of echoes emanating from surrounding tissues (cardiac muscle, parenchyma of an organ, or the like).

In order to accomplish the above object, a diagnostic ultrasound system in accordance with the present invention is constructed as described below.

The present invention attempts to adapt a Doppler technique to a contrast echo technique that is based on the nonlinear scattering characteristic of bubbles constituting an ultrasound contrast medium injected into a patient body and that is referred to as a "harmonic echo" technique. In the past, it has been unknown in what way the Doppler effect of a nonlinear component of an echo resulting from transmission of an ultrasound beam with a frequency $f_0$ is rendered qualitatively and quantitatively. The present inventor gave attention to a second harmonic serving as a component typical of nonlinear components, conducted experiments on evaluation of the Doppler effect on the second harmonic, and verified that the Doppler shift of the second harmonic was equivalent to a Doppler shift occurring when an ultrasonic wave of which frequency is the frequency of the second harmonic is transmitted and received. The present invention has been devised on the basis of this finding.

An ultrasound contrast medium is composed of minute bubbles. Echoes are enhanced due to the strong scattering characteristic of the bubbles. It is known that scattering of the bubbles exhibits a strong nonlinear characteristic. Using this characteristic, echoes emanating from any material other than the bubbles can be distinguished from echoes emanating from a contrast medium (bubbles). A more particular procedure will be described below.

(1) A harmonic occurs due to nonlinear scattering. Using this phenomenon, only a harmonic is received relative to a transmitted fundamental component. When consideration is taken into a tissue attenuation and a bandwidth permitted by a transmitting and receiving system, the usage of a second harmonic is especially effective.

(2) A subharmonic or its superharmonic occurs due to nonlinear scattering. Using this phenomenon, only a subharmonic or a superharmonic is received relative to a transmitted fundamental component.

Assuming that the frequency of a transmitted fundamental component is $f_0$, when the frequency of a harmonic, subharmonic, or superharmonic is expressed as $\alpha f_0$, a moving velocity of a contrast medium is detected by calculating the following conversion expression:

$$v = V\cos\theta = Cf_d/2(\alpha f_0 + f_d)$$

or the following proximate conversion expression based on the fact that a moving velocity of an object is lower than a sound velocity:

$$v = V\cos\theta = Cf_d/2\alpha f_0$$

where C denotes a sound velocity, V denotes a moving velocity of an object, v denotes a component of a moving velocity in a direction of an ultrasound beam, θ denotes an angle of an ultrasound beam with respect to a moving direction of an object, $f_0$ denotes a transmission frequency, and $f_d$ denotes a Doppler shift. Herein, the transmission frequency means a carrier frequency of a pulser or a center frequency (center of a bandwidth) or peak frequency in a transmitted sound pressure spectrum.

In this mode, it is very important that a nonlinear component expressed as of $\alpha f_0$ is not included in the transmission frequency band.

According to one aspect of a diagnostic ultrasound system of the present invention, an ultrasound probe is driven to transmit an ultrasound beam to a patient and to perform beam forming on echoes that are quantities of electricity output from the ultrasound probe. A Doppler shift of a nonlinear component of an echo attributable to reflection of an ultrasound beam by an ultrasound contrast medium injected into a patient body is sampled from the echo. The Doppler shift $f_d$ is converted into a velocity component v according to the following conversion expression:

$$V = V\cos\theta = Cf_d/2f_{set} + f_d$$

where C denotes a sound velocity, V denotes a moving velocity of a moving object in a patient body, v denotes a component of a moving velocity V in a direction of an ultrasound beam, θ denotes an angle of an ultrasound beam with respect to the moving direction of an object, $f_{set}$ denotes a set frequency used for velocity conversion, and $f_d$ denotes a Doppler shift. Preferably, the set frequency $f_{set}$ is the frequency of a reference signal used in the system, which is set outside a frequency band of the ultrasound beam being transmitted. Thereafter, velocity information concerning a moving object in the patient body is displayed on the basis of the velocity component v.

According to another aspect of the present invention, there is a diagnostic ultrasound system whereby an object including a moving constituent therein is scanned by a ultrasound beam signal in a contrast echo technique, based on a Doppler technique, in which an ultrasound contrast medium is injected into the object to be placed in the moving constituent, the system comprising: a unit for driving an ultrasound probe in order to transmit the ultrasound beam signal toward the object; a unit for acquiring an echo signal echoed from the ultrasound contrast medium on the basis of an ultrasound echo signal received by the ultrasound probe; a unit for evaluating information of a Doppler shift frequency concerning a nonlinear component of the echo signal on the basis of a reference signal of which frequency is set outside a frequency band of the ultrasound beam signal being transmitted; and a unit for visualizing the evaluated information of the Doppler shift frequency.

Still another aspect of the present invention is that there is provided a method of ultrasound imaging whereby an object including a moving constituent therein is scanned by a ultrasound beam signal in a contrast echo technique, based on an Doppler technique, in which an ultrasound contrast medium is injected into the object to be placed in the moving constituent, the method comprising the steps of: driving an ultrasound probe in order to transmit the ultrasound beam signal toward the object; acquiring an echo signal echoed from the ultrasound contrast medium on the basis of an ultrasound echo signal received by the ultrasound probe; evaluating information of a Doppler shift frequency concerning a nonlinear component of the echo signal on the basis of a reference signal of which frequency is set outside a frequency band of the ultrasound beam signal being transmitted; and visualizing the evaluated information of the Doppler shift frequency.

DETAILED DESCRIPTION OF THE PREFERRED EMBODIMENTS

An embodiment of the present invention will be described below in conjunction with the drawings.

An embodiment will be described in conjunction with FIGS. 1 to 8. A diagnostic ultrasound system in accordance with this embodiment adopts a contrast echo technique making it possible to efficiently detect second harmonics stemming from nonlinear scattering of bubbles contained in an ultrasound contrast medium, to display a distribution of the bubbles two-dimensionally, and to perform measurement by utilizing the Doppler effect.

Figure 1:
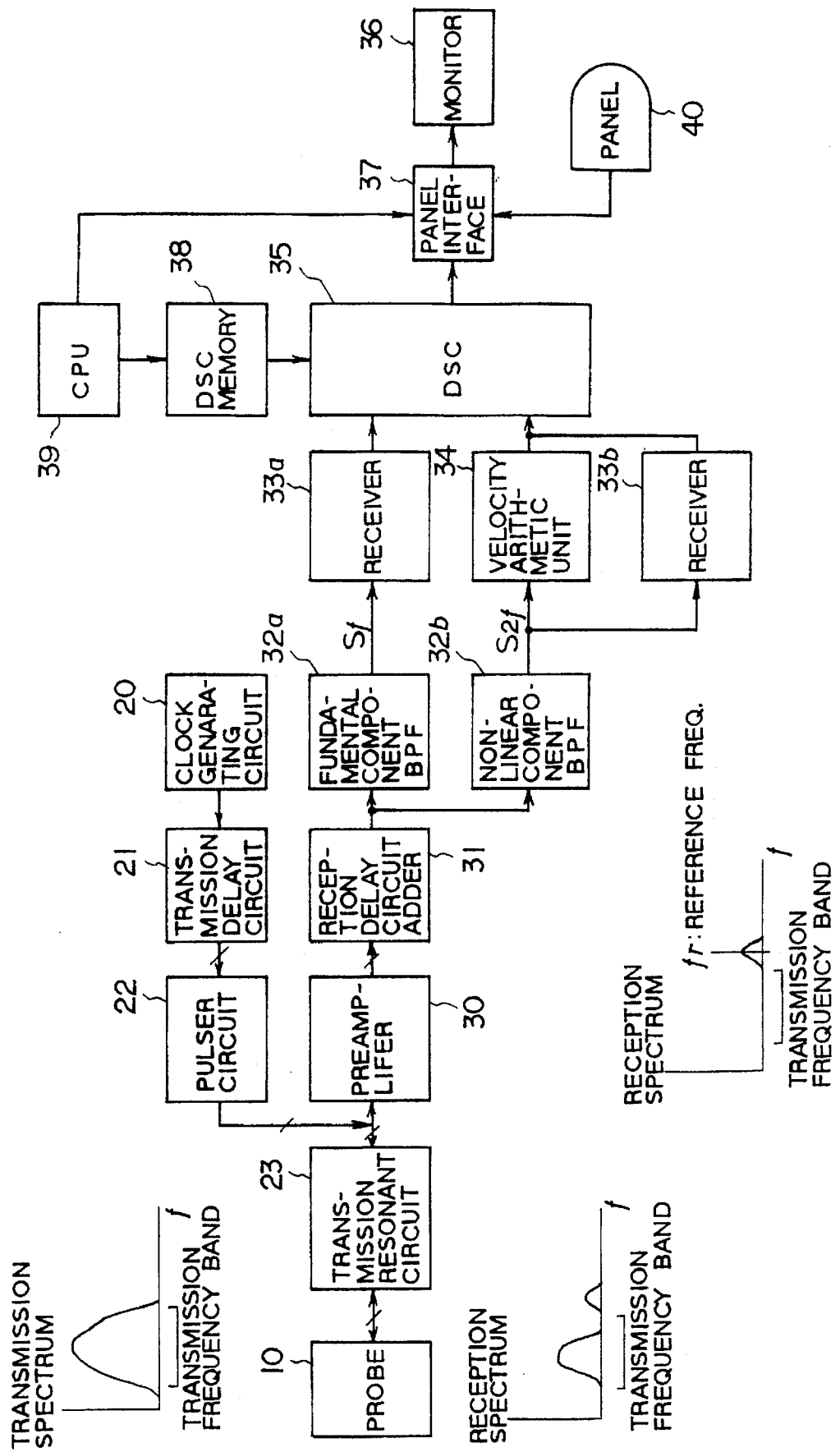
FIG. 1 is a block diagram of a diagnostic ultrasound system in accordance with an embodiment of the present invention.

As shown in FIG. 1, the diagnostic ultrasound system comprises an ultrasound probe 10 for transmitting and receiving ultrasonic waves to or from a patient body, and a main unit 11 for driving the ultrasound probe 10 and processing received signals of the ultrasound probe 10.

The ultrasound probe (hereinafter probe) 10 is of a phased-array type in which a plurality of transducers are arranged in a direction of scanning. The transducers possess the same reception characteristic, and have a sufficiently wide passband permitting detection of a fundamental component for driving each transducer and a second harmonic produced by a living body.

The main unit 11 includes such circuits as a transmitting system for driving the probe 11, a receiving and processing system for receiving and processing signals sent from the probe 10, a display system for displaying processed images, and an input system. In addition, a detecting system for detecting a biomedical signal such as an echocardiographic signal is included but is not shown in the drawing.

The transmitting system includes a clock generating circuit 20, a transmission delay circuit 21, a pulser circuit 22, and a transmission resonant circuit 23. The clock generating circuit 20 is a circuit for generating a clock used to determine the timing of transmitting an ultrasonic wave and a transmission frequency. The transmission delay circuit 21 is a circuit for performing transmission focusing by delaying transmission waves. The pulser circuit 22 includes the same number of pulsers as the number of individual paths (hereinafter channels) associated with the transducers, generates a driving pulse according to the timing of each delayed transmission wave, and supplies the driving pulse to each transducer.

Figure 2:
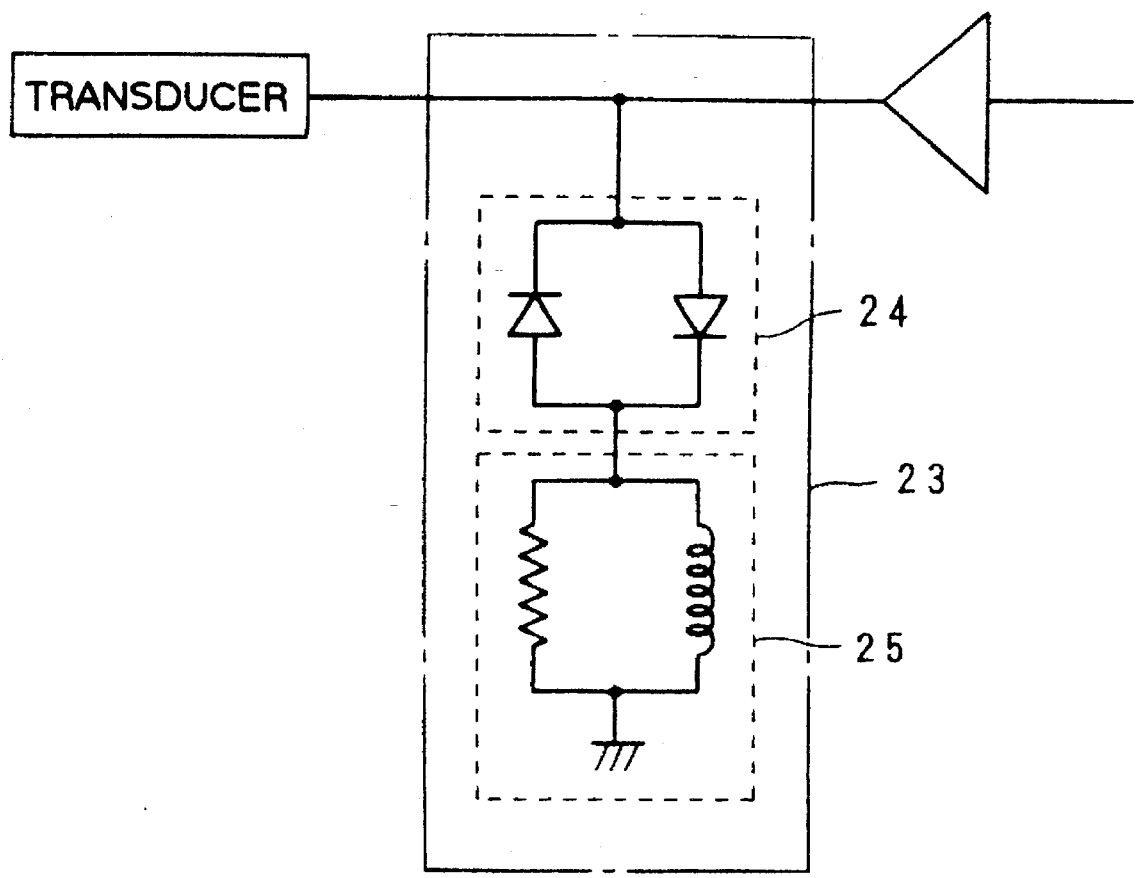
FIG. 2 is a circuit diagram showing an example of a transmission resonant circuit.

The transmission resonant circuit 23 is one of the constituent features of the diagnostic ultrasound system, and is included in order to efficiently detect, for example, second harmonics of echoes stemming from an ultrasound contrast medium injected into a living body. In other words, the diagnostic ultrasound system includes a facility capable of removing harmonics at the time of transmission. The transmission resonant circuit 23 includes, as shown in FIG. 2, a limiter 24 formed with a diode inverse parallel circuit and a coil unit 25 that becomes resonant with a capacitive impedance of a probe, cable, or the like and offers a passband centered on a fundamental frequency alone. The limiter 24 is turned on when an applied signal has a certain level or higher. The transmission resonant circuit 23 becomes therefore resonant only during transmission during which an applied signal level is high, and remains non-resonant during reception. The series circuit composed of the limiter 24 and coil unit 25 is installed for each channel in practice.

Furthermore, the receiving and transmitting system includes, for example, a preamplifier 30, a reception delay circuit adder 31, bandpass filters (BPF) 32a and 32b, receivers 33a and 33b, and a velocity arithmetic unit 34 in that order on the output stage of the probe 10. The preamplifier 30 amplifies power of a received echo for each channel, and sends the results to the reception delay circuit adder 31. The reception delay circuit adder 31 includes delay circuits associated with the reception channels and an adder for adding up delayed results, and performs reception focusing on the received echoes. Connected on the output stage of the reception delay circuit adder 31 are the bandpass filters 32a and 32b for handling the fundamental component and nonlinear component respectively and connected in parallel.

The passband of the fundamental component bandpass filter 32a agree with the frequency of a fundamental component of an echo. By contrast, the passband of the nonlinear component bandpass filter 32b agrees with the frequency of a second harmonic of the echo. The output stage of the fundamental bandpass filter 32a is connected to a digital scan converter (DSC) 35, which will be described later, via the fundamental component receiver 33a, while the output stage of the nonlinear component bandpass filter 32b is connected to the DSC 35 via the nonlinear component receiver 33b. These two receivers 33a and 33b are receiving circuits for performing such processing as envelope detection, logarithmic compression, or the like on each fundamental component or second harmonic, and for producing a B-mode image signal.

Furthermore, the receiving and processing system includes the digital scan converter (DSC) 35 and a monitor 36. The DSC 35 includes an A/D converter for handling an output of a receiver, a multiplexer, a frame memory, a writing and reading circuit, and a D/A converter, and produces a one-frame image signal conformable to a commanded display mode. The image signal can then be read according to a standard TV system. The image signal read from the DSC 35 is output to and displayed on the monitor 36 via a panel interface 37.

Furthermore, a CPU 39 is connected to the DSC 35 via a DSC memory 38.

The input system in the diagnostic system includes the panel interface 37 and a panel 40 manipulated by an operator.

Figure 3:
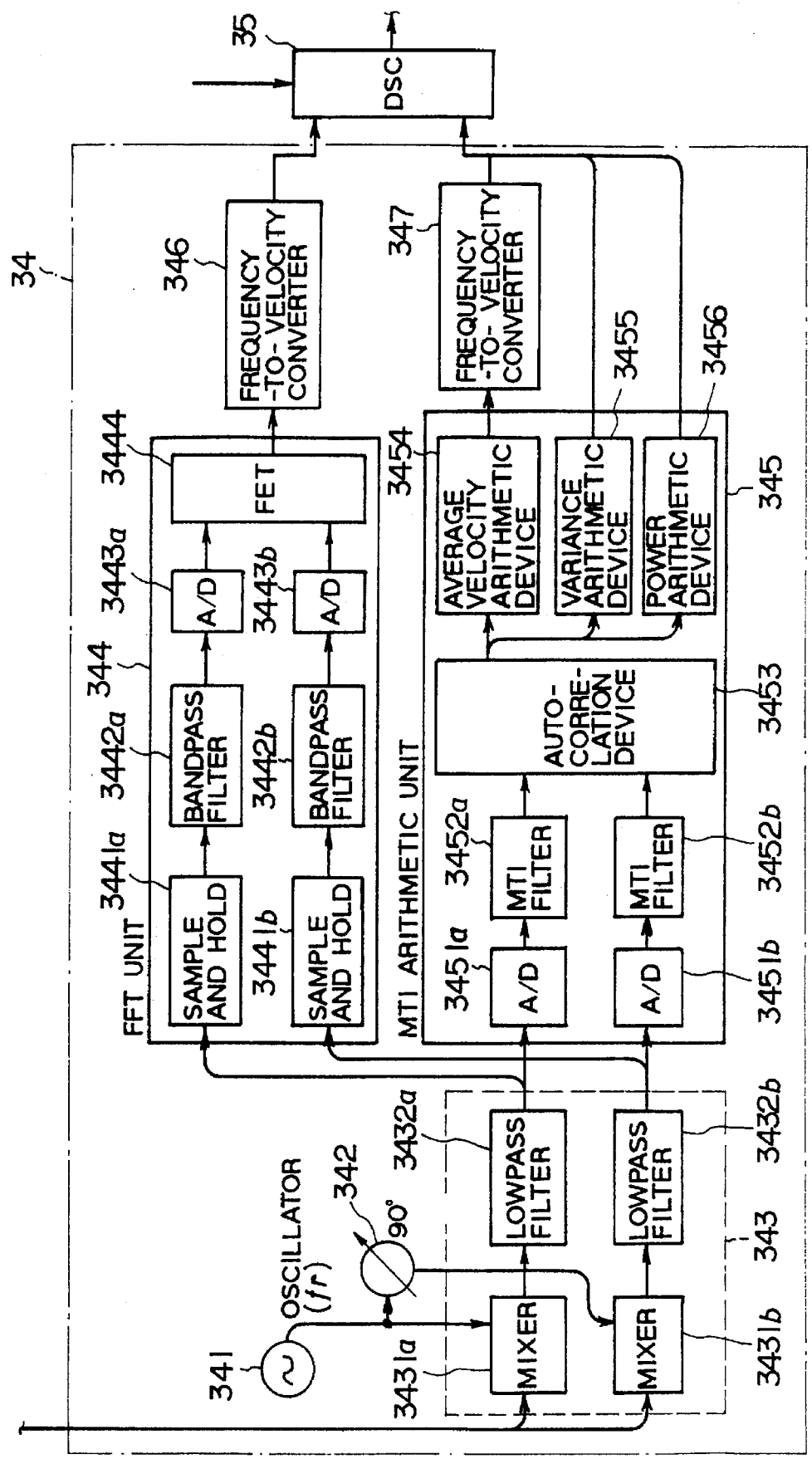
FIG. 3 is a block diagram of a velocity arithmetic unit.

The velocity arithmetic unit 34 detects a velocity of an ultrasound contrast medium injected into a patient body. An example of the circuitry of the velocity arithmetic unit 34 is shown in FIG. 3.

The velocity arithmetic unit 34 illustrated includes a reference oscillator 341, a 90° phase shifter 342, a phase detector 343, a fast Fourier transform (FFT) arithmetic unit 344, an MTI arithmetic unit 345, and first and second frequency-to-velocity converters 346 and 347. The reference oscillator 341 outputs a reference signal (reference frequency $f_r$) used to detect a (orthogonal) phase of an echo that has been subjected to beam forming. The 90° phase shifter 342 shifts the phase of an input signal accurately by 90° and outputs a resultant signal. The phase detector 343 includes two channels of series circuits composed of mixers 3431a and 3231b and lowpass filters 3432a and 3432b (the cutoff frequency fc is set equally to the reference frequency $f_r$). One of the mixers that is a mixer 3431a receives a reference signal directly, and the other mixer 3431b receives the reference signal via the phase shifter 342. Owing to this circuitry, an echo passing through the nonlinear component bandpass filter 32b is subjected to orthogonal detection by the phase detector 343, and then supplied to the FFT arithmetic unit 344 and MTI arithmetic unit 345.

The FFT arithmetic unit 344 includes two channels of processing circuits composed of sample and holds 3441a and 3441b, bandpass filters 3442a and 3442b, and A/D converters 3443a and 3443b. The FFT arithmetic unit 344 further includes a frequency analyzer 3444 for performing fast Fourier transform (FFT) on receipt of the processed data. Owing to this circuitry, only a Doppler signal returning from any depth is sampled from phase-detected echoes by the sample and holds, and unwanted components are removed by the bandpass filters 3442a and 3442b. The frequency of the Doppler signal is analyzed in real time directly by the frequency analyzer 3444.

On the other hand, the MTI arithmetic unit 345 includes two channels of circuits composed of A/D converters 3451a and 3451b and MTI filters 3452a and 3452b, an autocorrelation device 3453, an average velocity arithmetic device 3454, a variance arithmetic device 3455, and a power arithmetic device 3456. Owing to this circuitry, after phase-detected echoes are converted into a digital form, unwanted permanent echoes emanating from cardiac walls or the like are removed by the MTI filters 3452a and 3452b. Thereafter, the echo data is subjected to frequency analysis (Doppler analysis), which analyzes the frequencies at respective points on a planar tomographic section, by the autocorrelation device 3453. Using Doppler shifts $f_d$ resulting from this analysis, an average of the Doppler shifts occurring at the points on the tomographic section is computed by the average velocity arithmetic device 3454. Similarly, a variance (spectral disorder level) and power (strength) are computed by the arithmetic devices 3455 and 3456 respectively.

In other words, the FFT arithmetic unit 344 and MTI arithmetic unit 345 detect Doppler shifts caused by a contrast medium moving through a vessel. The FFT arithmetic unit 344 is actuated in spectral Doppler mode, and the MTI arithmetic unit 345 is actuated in color Doppler mode.

Analytic data provided by the FFT arithmetic unit 344 is supplied to the DSC 35 via a first frequency-to-velocity converter 346, and arithmetic data provided by the average velocity arithmetic device 3454 in the MTI arithmetic unit 345 is supplied to the DSC 35 via a second frequency-to-velocity converter 347.

The first and second frequency-to-velocity converters 346 and 347 embody the constituent feature of the present invention, and convert the dimension of a Doppler shift $f_d$ into the dimension of a corresponding velocity v; that is, a moving velocity of a contrast medium (bubbles) according to the conversion expression described below.

In this embodiment, the reference frequency $f_r$ reported to the mixer 3431a or 323b in the phase detector 343 is agreed with the frequency of a second harmonic $2f_0$ relative to a transmission frequency $f_0$. The reference frequency $f_r$ and second harmonic $2f_0$ are regarded as a set frequency $f_{set}$ used for velocity conversion in accordance with the present invention.

The Doppler shift $f_d$ is converted into a component v of a moving velocity in a direction of an ultrasound beam according to the following expression:

$$v = V\cos\theta = Cf_d/(2\alpha f_0 + f_d) \quad (1)$$

wherein α equals to 2, C denotes a sound velocity, V denotes a moving velocity of an object, θ denotes an angle of an ultrasound beam with respect to the moving direction of an object, $f_0$ denotes a transmission frequency, and $f_d$ denotes a Doppler shift.

Alternatively, the conversion is achieved according to the following proximate expression based on the fact that the moving velocity of an object (bubbles) is lower than the sound velocity:

$$v = V\cos\theta = Cf_d/2\alpha f_0 \quad (2)$$

The transmission frequency $f_0$ basically refers to a carrier frequency of a pulser, a center frequency (center of a bandwidth) or peak frequency in a transmission sound pressure spectrum.

When a second harmonic s adopted as an object nonlinear component, the coefficient of conversion a should preferably range from 1.5 to 2.0 in consideration of a biomedical decay or the like. Likewise, when a subharmonic is adopted, the coefficient α should preferably be 0.7 or smaller. When all harmonics are used, the coefficient a should be a natural number except 1.

In the present invention, it is essentially important that the reference frequency $f_r$ is not included in a transmission frequency band. The transmission frequency band is, as shown in FIG. 4B, comparable to a band centered on a peak frequency of an ultrasonic wave to be transmitted by the ultrasound probe 10, and usually has a level of −20 dB or larger in relation to the peak frequency. In this system, even when the reference frequency $f_r$ is equal to the frequency of a second harmonic $2f_0$, unless the above condition is satisfied, it does not make sense. This is because it becomes impossible in a received signal to discriminate a second harmonic caused by a contrast medium from an echo of a second harmonic contained in a transmission signal which is reflected from a surrounding organ. Consequently, an effect expected from this system cannot be exerted.

Figure 5:
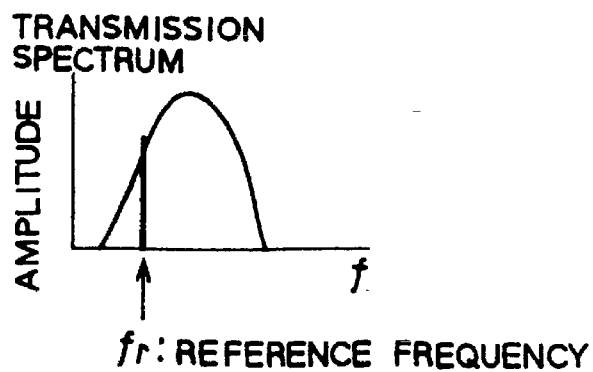
FIG. 5 is a diagram showing an example of a relationship between a transmission spectrum and reference frequency.

As shown in FIG. 5, even in some known Doppler unit, a so-called transmission frequency and reference frequency are set to differ from each other in this case, the reference frequency is set to be lower than a peak frequency of a transmission signal in consideration of a tissue attenuation. It is essentially important that the reference frequency is within the transmission frequency band. The set frequency $f_{set}$ used for velocity conversion in accordance with the present invention may be, as described above, defined using either of the transmission frequency $f_0$ or reference frequency $f_r$.

When nonlinearly-scattering echoes reflected from a contrast medium, which are a precondition of this system, are not used as an object, even if a reference frequency is set outside a transmission frequency band and observed Doppler shifts are converted into velocities according to the conversion expression (1) or (2), it does not make sense. The Doppler effect varies depending on a transmission frequency. A transmission frequency $f_0$ that does not undergo a shift and a Doppler shift $f_d$ have the following simple relationship:

$$f_d = (2V\cos\theta/C)f_0$$

Conversion becomes meaningless unless the frequency $f_0$ that does not undergo a shift is used. That is to say, $$v = V\cos\theta = Cf_d/2f_0$$

Basically, in the known pulsed Doppler techniques, the Doppler effect is convoluted to all frequency components within a frequency band of a transmission signal. It is the best way in terms of velocity precision that a reference frequency is set equally to the peak frequency of the transmission signal. In a pulsed Doppler technique in accordance with this system, it is the best way in terms of velocity precision that any of the frequency bands of nonlinear components (harmonic, subharmonic, and superharmonic) which are outside the frequency band of the transmission signal is selected, and that a reference frequency is set equally to a peak frequency of a received signal having the frequency band.

As mentioned above, (data converted into the dimension of a velocity by the first or second frequency-to-velocity converter 346 or 347 is sent together with the other necessary data to the DSC 35, and converted into frame image data conformable to a commanded display mode. A color processing circuit and a D/A converter are incorporated in the panel interface 37. The image data provided by the DSC 35 is colored if necessary, and sent as an analog signal to the monitor 36. A recorder, memory, or any other external unit may be connected in place of or in parallel with the monitor 36.

The CPU 39 reads a command entered by an operator manipulating the panel 40 via the panel interface 37, outputs a superposition display marker or character data from the DSC memory 38 to the DSC 35, and performs velocity measurement.

Next, the operations and advantages of this embodiment will be described.

Figure 4A:
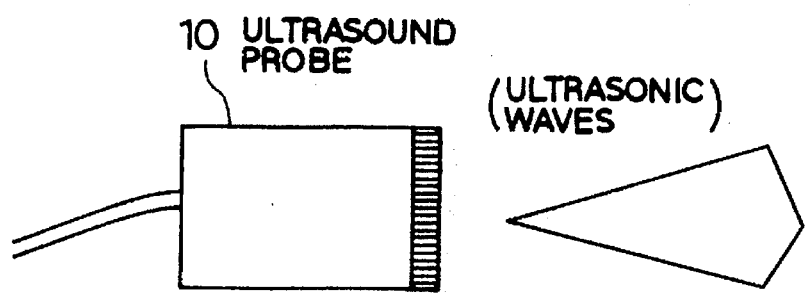
FIGS. 4A and 4B are diagrams showing an ultrasound probe and a transmission spectrum.
Figure 4B:
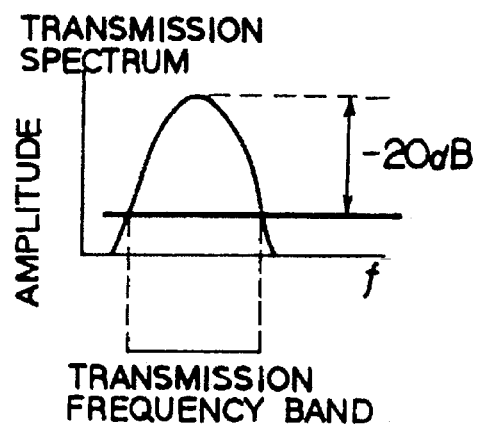

During transmission as illustrated in FIG. 4A, a driving voltage is supplied for each channel from the pulser circuit 22 to the transducers in the probe 10 via the transmission resonant circuit 23 with transmission focusing effected by the transmission delay circuit 21. At this time, the limiter in the transmission resonant circuit 23 is kicked on because the driving voltage is higher than a given level, and a resonator 24 gets resonant. With this resonance, only a fundamental component of the driving voltage passes through the transmission resonant circuit 23 and enters each transducer in the probe 10.

It is practically very hard to drive the pulser circuit 22 with a perfect sine wave. Normally, a driving voltage generated by the pulser circuit contains harmonics. The harmonics are intentionally cut off by the transmission resonant circuit 23. Each transducer is excited with a driving voltage containing only a fundamental component.

When the transducers in the probe 10 are thus excited, an ultrasound beam that has been subjected to transmission focusing is transmitted to a diagnostic region such as the cardiac muscle of a patient body. The ultrasound beam is reflected and scattered as ultrasound echoes from an ultrasound contrast medium (for example, the aforesaid product by the name of "Albunex injection 5 ml") that has been injected intravenously to tissues in the diagnostic region. In particular, since the ultrasound contrast medium is composed of minute bubbles, the echoes are enhanced owing to the strong scattering characteristic exhibited by the bubbles. The scattering exhibits a nonlinear characteristic. The scattering of the nonlinear characteristic causes harmonics. As a result, the ultrasound echoes each contain an echo component emanating from a living tissue except the contrast medium (bubbles) and echo components (fundamental component and its harmonics) emanating from the contrast medium.

The ultrasound echoes are received by the transducers in the probe 10 and converted into corresponding electrical signals. Since the powers of the echoes that are quantities of electricity are very weak, the limiters 24 in the transmission resonant circuit 23 are not kicked on. The transmission resonant circuit 23 remains nonresonant. As a result, the echoes each containing a fundamental component and harmonics reach the preamplifier 30 without any interruption by the transmission resonant circuit 23, and are then amplified in power. Thereafter, the echoes are received and delayed channel by channel by the reception delay circuit adder 31, and then added up thereby. Thus, the echoes are subjected to reception focusing. The resultant received echo is sent concurrently to the fundamental component BPF 32a and nonlinear component BPF 32b. The fundamental component BPF 32a samples a fundamental component $S_f$ of the echo, and sends the fundamental component to the receiver 33a on the succeeding stage. The nonlinear component BPF 32a samples only a second harmonic $S_{2f}$ of the echo, and sends the second harmonic to the receiver 33b and velocity arithmetic unit 34.

The echo of the fundamental component Sf sent to the receiver 33a is subjected to envelope detection, logarithmic compression, or any other processing, whereby B-mode image data represented by the fundamental component (enhancement-modulated image showing amplitudes) is produced. The echo of the second harmonic $S_{2f}$ sent to the other receiver 33b is subjected to the same processing, whereby B-mode image data represented by the second harmonic is produced.

Figure 6:
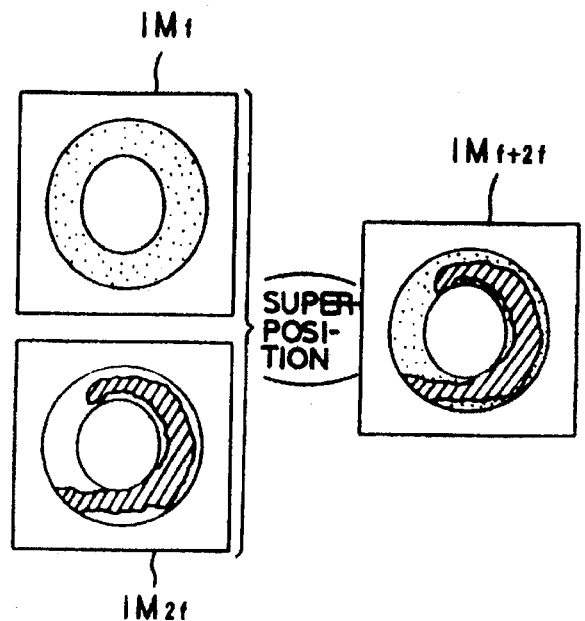
FIG. 6 is a diagram showing an example of a tomographic image produced in this embodiment.

These B-mode image data items represented by the fundamental component and second harmonic are then converted into image data items conformable to a commanded display mode by the DSC 35. Various display modes are available for a B-mode image $IM_f$ represented by a fundamental component (hereinafter, simply, a fundamental component image) and for a B-mode image $IM_{2f}$ represented by a second harmonic (hereinafter, simple, a second harmonic image). At the time when contrast echo imaging is implemented, for example, a display mode in which the second harmonic image $IM_{2f}$ is superposed on the fundamental component image $IM_f$ is commanded. The DSC 35 synthesizes the image data items accordingly and supplies resultant data to the monitor 36. An image $IM_{f+2f}$ made by superposing the second harmonic image $IM_{2f}$ on the fundamental component image $IM_f$ is therefore, as shown in FIG. 6, displayed on the monitor 36. Consequently, the morphology of a living tissue and the distribution of a contrast medium within the tissue can be observed.

As mentioned above, in this embodiment, harmonics other than a fundamental component are cut off intentionally (actively) by the transmission resonant circuit 23, whereby an ultrasound beam containing only the fundamental component is transmitted. A second harmonic contained in an echo stems substantially from the nonlinear scattering characteristic of an ultrasound contrast medium. In other words, when ultrasonic waves each containing only a fundamental component are transmitted, only second harmonics stemming from scattering of a contrast medium can be selectively processed for imaging. The second harmonic can therefore be utilized effectively in terms of a tissue attenuation or the bandwidth of a transmitting and receiving system.

Figure 7:
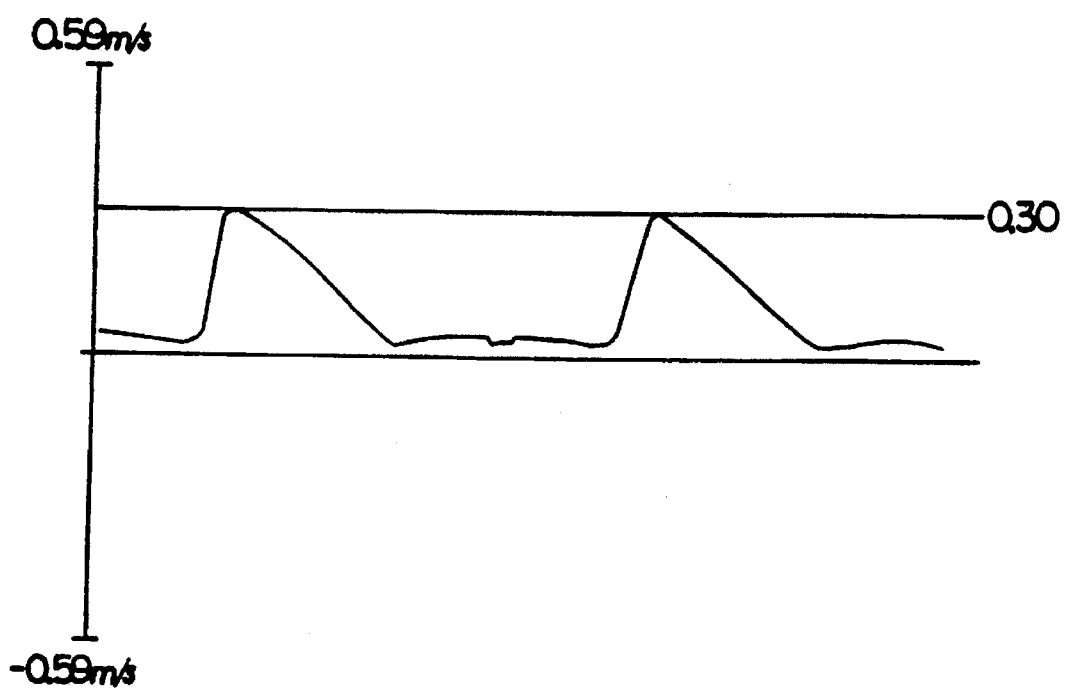
FIG. 7 is a diagram showing an example of a Doppler spectrum.

Furthermore, in this embodiment, when a spectral Doppler mode is commanded, the FFT arithmetic unit 344 in the velocity arithmetic unit 34 performs FFT as mentioned above. The analytic data is converted into velocity data v by the first frequency-to-velocity converter 346. The velocity data v is, for example, as shown in FIG. 7, displayed as a spectral Doppler image that depicts enhancement-modulated velocity information with gray scale. By contrast, when a color Doppler mode is commanded, the MTI arithmetic unit 345 in the velocity arithmetic unit 34 performs frequency analysis as mentioned above. The analytic data is converted into velocity data v by the second frequency-to-velocity converter 347. The data v is, for example, as shown in FIG. 8, displayed as a color Doppler image depicting color-modulated velocity information.

In the spectral Doppler image shown in FIG. 7, the axis of ordinates serves as an axis of velocities (axis of frequencies: a velocity scale), and the axis of abscissae serves as an axis of times. The axis of velocities indicates values given by the aforesaid velocity conversion expression. For example, detected values of a maximum velocity are indicated on the scale. When any measurement facility is employed, as illustrated, a peak velocity or the like can be calculated according to the aforesaid velocity conversion expression and then displayed. At this time, as shown in FIG. 1, a command entered at the operation panel 40 is sent to the CPU 39 via the panel interface 37. Measured data is then displayed on the monitor 36 by means of the DSC 37 and DSC memory 38 under the control of the CPU. Memory information or the like is also displayed on the monitor 36 by means of the DSC 37 and DSC memory 38.

Figure 8:
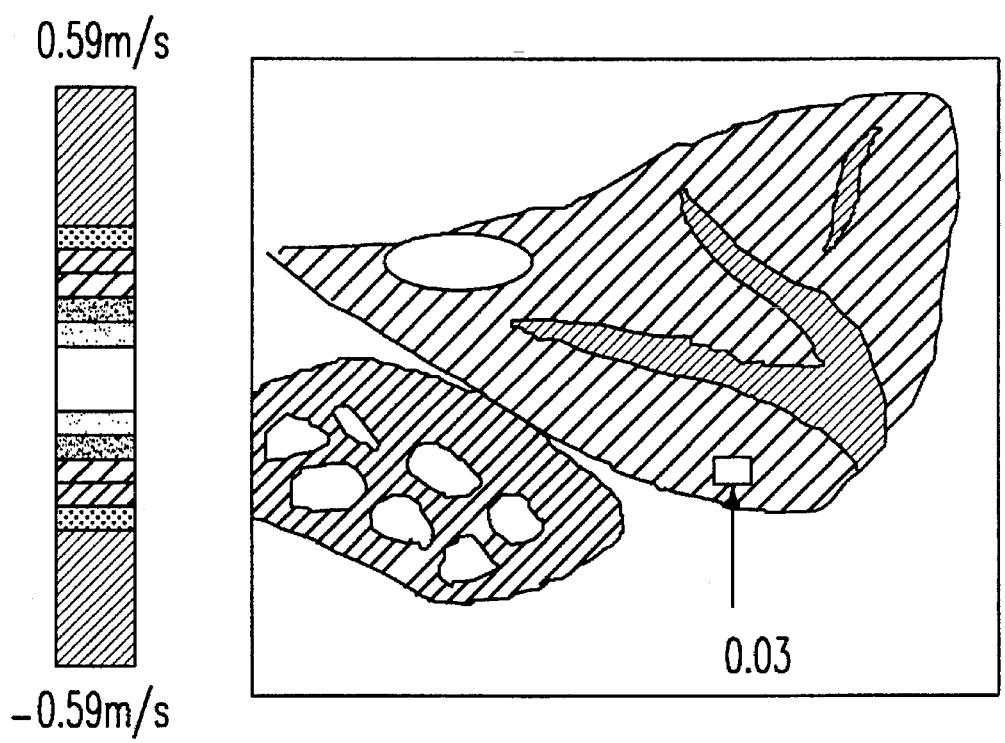
FIG. 8 is a diagram showing an example of a color Doppler image.

By contrast, in the color Doppler image shown in FIG. 8, colors are given according to a color map created using the aforesaid conversion expression. Together with a color bar or color palette, velocity values given by the velocity conversion expression are displayed on a scale or within a desired ROI available when the measurement facility is employed.

As mentioned above, a contrast echo technique using a contrast medium has been developed into a harmonic echo technique based on the nonlinear scattering characteristic of bubbles constituting a contrast medium. Furthermore, when Doppler imaging is performed on the basis of the harmonic echo technique, a set frequency $f_{set}$ used to convert a Doppler shift $f_d$ into a velocity v is set with confidence so that it becomes equal to a reference frequency $f_r$, which is equal to $2f_0$, on the basis of the experimental verification that a Doppler shift is equivalent to a Doppler shift occurring when a second harmonic is transmitted and received. As a result, even a blood flow that is low in velocity and minute in size; such as, a tissular blood flow or myocardial blood flow, can be detected with a high signal-to-noise ratio. The velocity can be measured highly precisely. In particular, when color Doppler imaging (CDI) is used to examine the abdomen, motion artifacts can be minimized and high-quality CDI images can be produced.

Figure 9:
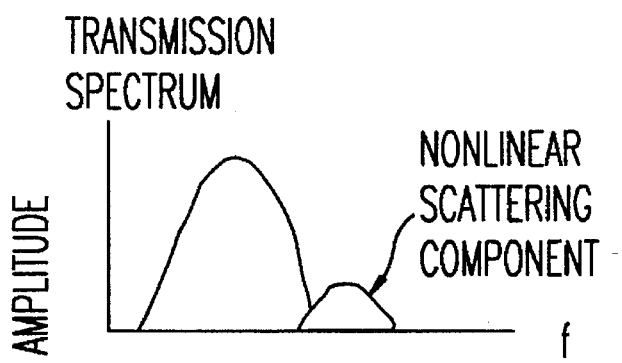
FIG. 9 is a diagram showing an example of a relationship between a transmission spectrum and nonlinear scattering component.

By the way, in the embodiment shown in FIG. 1, a transmission frequency component is reflected relatively strongly from a surrounding tissue. Echoes nonlinearly scattered by a contrast medium in vessels in tissues are, as shown in FIG. 9, thought to be depicted outside a fundamental frequency band on a spectrum of received echoes. This means that a reference frequency can be set outside the fundamental frequency band of a signal received by an ultrasound probe. However, as seen in a diagnostic ultrasound system shown in FIGS. 10 and 11A, 11B, when the frequency characteristic of each receiving transducer is relatively low sensitivity to a fundamental component of a transmission signal, the same cannot apply. A phased-array type probe 10 in a diagnostic ultrasound system shown in FIG. 10 has two groups of transducers A and B. The frequency band for each of transducers $10_1, 10_3$, etc., and $10_{n-1}$ of the group A is set to become responsive substantially only to a fundamental component f (See FIG. 11A). The frequency band for each of transducers $10_2, 10_4$, etc., and $10_n$ of the group B is set to become responsive substantially only to a second harmonic $2f$ (See FIG. 11B). These frequency bands are determined by, for example, changing resonance frequencies of transducers group by group.

When the probe 10 is structured as mentioned above, ultrasonic waves each containing a fundamental component alone are transmitted and received by the group A of transducers. Echoes each containing a fundamental component $S_f$ alone are provided directly by a preamplifier 30a and reception delay circuit adder 31a which are connected to the group A of transducers. Likewise, echoes each containing only a second harmonic $S_{2f}$ of nonlinear components stemming from nonlinear scattering of an ultrasound contrast medium are received by the group B of transducers, and provided directly by a preamplifier 30b and reception delay circuit adder 31b.

Figure 10:
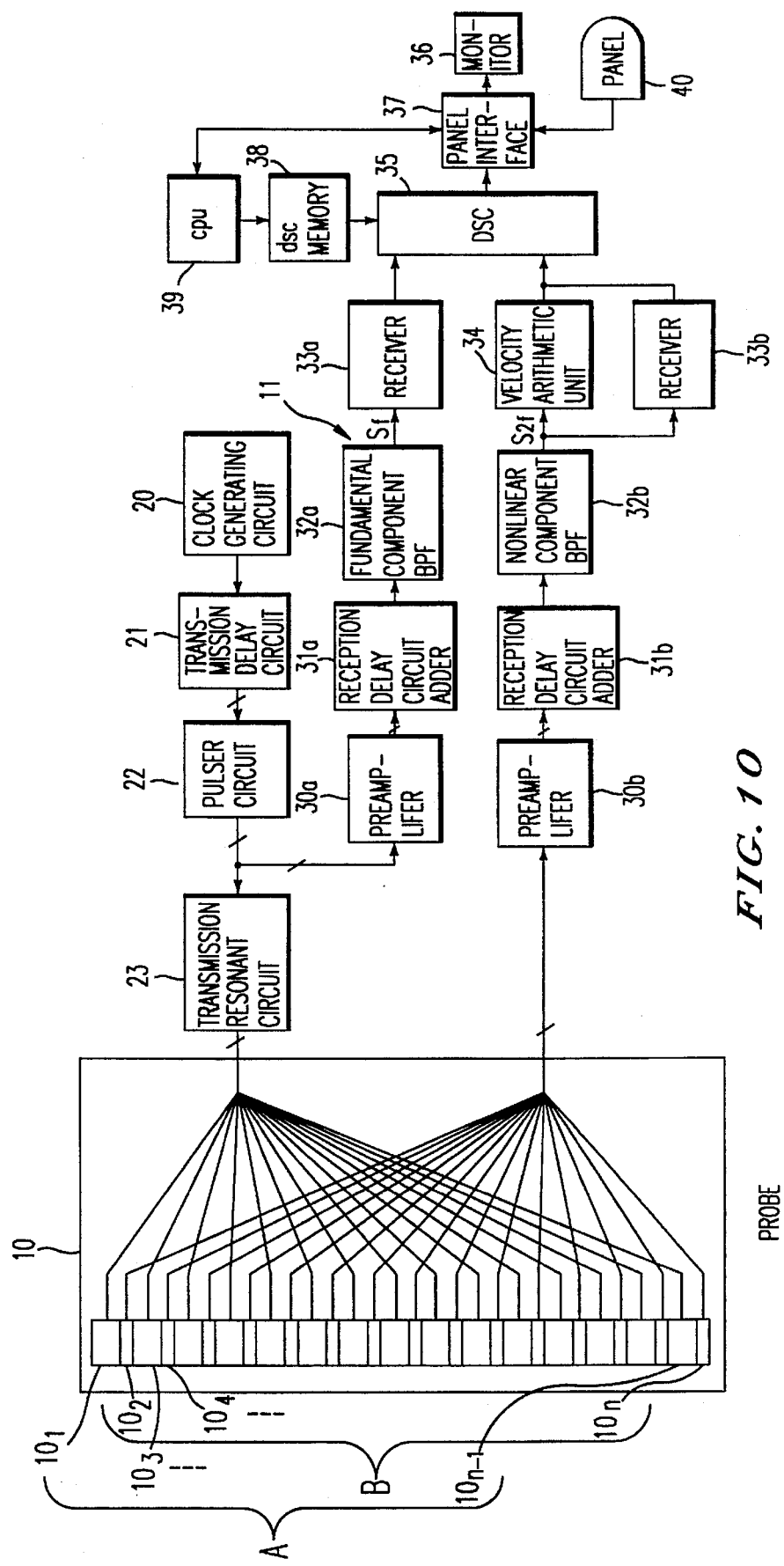
FIG. 10 is a block diagram of a diagnostic ultrasound system in accordance with a variant.
Figure 11A:
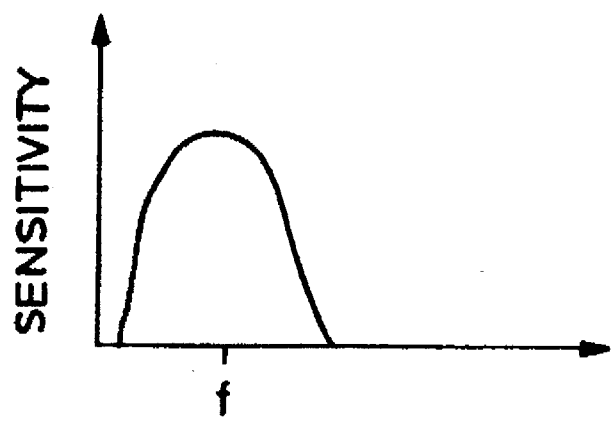
FIGS. 11A and 11B are graphs showing frequency characteristic curves concerning respective groups of transducers.
Figure 11B:
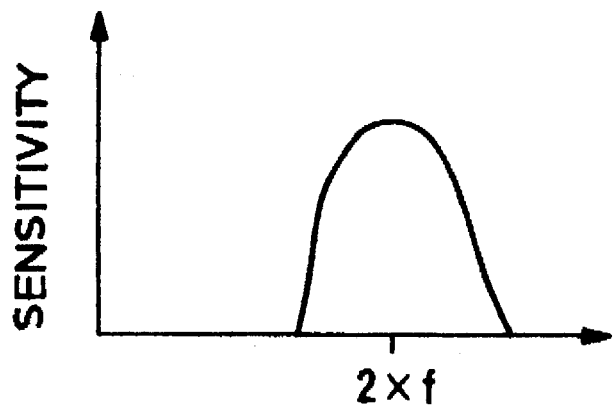

In the configuration shown in FIG. 10, the transmission resonant circuit 23 and BPFs 32a and 32b may be excluded. The other components and functions are similar to or identical to those shown in FIG. 1.

In the aforesaid embodiment, a second harmonic is taken for instance as a nonlinear component to be sampled. The present invention is not necessarily limited to the second harmonic. For example, any other harmonic; such as, an N-th harmonic (N×f where f denotes a fundamental frequency and N denotes a positive integer), an N-th subharmonic (f/N where f denotes a fundamental frequency and N denotes a positive integer), and a superharmonic (M×f/N where f denotes a fundamental frequency, and M and N each denote a positive integer of 1 or larger) may be adopted so that they are selectively sampled by a nonlinear component BPF in the same manner as mentioned above. For handling a plurality of harmonics concurrently, the same number of signal sampling and processing systems as the number of the harmonics may be installed independently or circuitry for passing a plurality of nonlinear components in an unseparated manner through one system may be adopted.

In the aforesaid embodiment, the circuitry is such that a fundamental component and nonlinear component are processed by separate systems. After received by a preamplifier, echoes may be digitized. On the succeeding stage, only one signal processing system may be installed so that signal processing can be performed on a fundamental component and nonlinear component on a time-sharing basis. Alternatively, a memory may be included so that a desired component can be processed.

In the aforesaid embodiment, the two BPFs for sampling a fundamental component and nonlinear component are inserted on the stage succeeding the reception delay circuit adder. Alternatively, the BPFs may be installed, for example, on the stage succeeding the preamplifier. However, when the BPFs are installed on the output stage of the reception delay circuit adder as those in the aforesaid embodiment, a smaller number of filters is needed. It is advantageous for avoiding the increase in size of the system or the rise in manufacturing cost.

Furthermore, a probe for the diagnostic ultrasound system is not limited to the electronic array probe but may be a mechanical scanning probe.

Furthermore, in the aforesaid embodiment, beam forming is performed on a radiofrequency (RF) signal. Alternatively, beam forming may be performed after the frequency band of the signal is shifted to an intermediate frequency.

In the aforesaid embodiment, a transmission system filter for passing a fundamental component alone or a transmission resonant circuit that attains series resonance may be used as a suppressing means for intentionally and actively suppressing nonlinear components.

Furthermore, a frequency-to-velocity converting means in accordance with the present invention is not limited to the aforesaid frequency-to-velocity converters 346 and 347. Alternatively, a memory feature having the same capability as the converters may be implemented in the frequency analyzer 3444 or autocorrelation device 3453. The memory feature may be implemented in the DSC 35.

The Doppler technique based on the harmonic echo technique can be summarized as follows: a set frequency used to convert a Doppler shift into velocity data can be optimized on the basis of the experimental verification that a Doppler shift is equivalent to a Doppler shift occurring when a second harmonic that is typical of nonlinear components is transmitted and received.

As a result, in a diagnostic ultrasound system utilizing the nonlinear scattering characteristic of a contrast medium, echoes generated under nonlinear scattering of a contrast medium can be used to measure the velocity of the contrast medium according to the Doppler principle. Moreover, (1) the velocity of a peripheral blood flow such as a myocardial blood flow or a blood flow in the parenchyma of the liver, which cannot be evaluated by the known contrast echo technique accompanied by intra-arterial injection because the moving velocity of a contrast medium does not reflect such a flow velocity, can be evaluated;

(2) the velocity of a peripheral blood flow in the cardiac muscle, the parenchyma of the liver, or the like which cannot be evaluated by the known contrast echo technique accompanied by intravenous injection because the concentration of a contrast medium becomes lower than that of a contrast medium injected intra-arterially, can be evaluated; and (3) motion artifacts stemming from the motions of surrounding tissues or the motions of vascular walls caused by respiration, which have been regarded as a factor of an error in precision in detection of a blood flow velocity in a vessel in the abdominal or the like in the past, can be minimized.

What is claimed is:

1. A diagnostic ultrasound system whereby an object including a moving constituent therein is scanned by an ultrasound beam signal in a contrast echo technique, based on a Doppler technique, in which an ultrasound contrast medium is injected into the object to be placed in the moving constituent, the system comprising:

an ultrasound probe for transmitting the ultrasound beam signal to the object and receiving an ultrasound signal echoed from the object in response to the transmitted ultrasound beam signal;

means for driving the ultrasound probe to transmit the ultrasound beam signal to the object;

means for processing an echoed output of the ultrasound probe into a beam-formed echo signal;

means for extracting from the echo signal a Doppler shift frequency of a nonlinear echo component resulting from the ultrasound beam signal reflected from the ultrasound contrast medium; and means for converting the Doppler shift frequency $f_d$ extracted by the extracting means into a velocity component v according to the following conversion expression:

$$V = V\cos\theta = Cf_d/(2f_{set} + f_d)$$

where C denotes a sound velocity, V denotes a moving velocity of the moving constituent in the object, v denotes a component of a moving velocity V in a direction of the ultrasound beam signal, $\theta$ denotes an angle of the ultrasound beam signal with respect to a moving direction of the moving constituent, $f_{set}$ denotes a set frequency used for velocity conversion, and $f_d$ denotes the Doppler shift frequency.

2. The system of claim 1, further comprising means for displaying information of the converted velocity component.

3. The system of claim 1, wherein the nonlinear echo component is a harmonic equal to a double of a transmission frequency of the ultrasound beam signal.

4. The system of claim 1, wherein the set frequency is a value made by multiplying a transmission frequency of the ultrasound beam signal by a coefficient.

5. The system of claim 4, wherein the coefficient is a value given as a rational number other than 1.

6. The system of claim 5, wherein the coefficient s a value residing in a range of 1.5 to 3.0.

7. The system of claim 4, where n the coefficient is a value of 0.7 or smaller.

8. The system of claim 4, where n the coefficient is a value given as a natural number other than 1.

9. The system of claim 1, wherein the set frequency is equal to a reference frequency employed in the diagnostic ultrasound system, the reference frequency being a value specified outside a range of a transmission frequency of the ultrasound beam signal.

10. The system of claim 9, wherein the reference frequency is a value made by multiplying the transmission frequency by a value given as a rational number.

11. The system of claim 9, wherein the reference frequency is a value residing in a range made by multiplying the transmission frequency by a value of 1.5 to 3.0.

12. The system of claim 9, wherein the reference frequency is a value residing in a range made by multiplying the transmission frequency by a value of 0.7 or smaller.

13. The system of claim 9, wherein the reference frequency is a value residing in a range made by multiplying the transmission frequency by a value given as a natural number other than 1.

14. The system of claim 13, wherein the natural number is 2.

15. The system of claim 1, wherein the set frequency is equal to a reference frequency employed in the diagnostic ultrasound system, the reference frequency being a value specified outside a fundamental frequency range of the echoed ultrasound signal received by the ultrasound probe.

16. The system of claim 15, wherein the reference frequency is a value made by multiplying a fundamental frequency in a spectrum of the echoed ultrasound signal by a value given as a rational number.

17. The system of claim 15, wherein the reference frequency is a value made by multiplying a fundamental frequency in a spectrum of the echoed ultrasound signal by a rational number of 1.5 to 3.0.

18. The system of claim 15, wherein the reference frequency is a value made by multiplying a fundamental frequency in a spectrum of the echoed ultrasound signal by a value of 0.7 or smaller.

19. The system of claim 15, wherein the reference frequency is a value made by multiplying a fundamental frequency in a spectrum of the echoed ultrasound signal by a value given by a natural number other than 1.

20. The system of claim 19, wherein the reference frequency is a value made by multiplying a fundamental frequency in a spectrum of the echoed ultrasound signal by 2.

21. The system of claim 1, wherein the converting means is a means that calculates the velocity component v using a following proximate conversion expression:

$$v = V\cos\theta = Cf_d/2 f_{set}$$

instead of the conversion expression.

22. A method of ultrasound imaging whereby an object including a moving constituent therein is scanned by an ultrasound beam signal in a contrast echo technique, based on a Doppler technique, in which an ultrasound contrast medium is injected in to the object to be placed in the moving constituent, the method comprising the steps of:

driving an ultrasound probe to transmit the ultrasound beam signal to the object, the ultrasound probe receiving an ultrasound signal echoed from the object in response to the transmitted ultrasound beam signal;

processing an echoed output of the ultrasound probe into a beam-formed echo signal;

extracting from the echo signal a Doppler shift frequency of a nonlinear echo component resulting from the ultrasound beam signal reflected from the ultrasound contrast medium; and converting the extracted Doppler shift frequency $f_d$ into a velocity component v according to the following conversion expression:

$$v = V\cos\theta = Cf_d/(2f_{set} + f_d)$$

where C denotes a sound velocity, V denotes a moving velocity of the moving constituent in the object, v denotes a component of a moving velocity V in a direction of the ultrasound beam signal, $\theta$ denotes an angle of the ultrasound beam signal with respect to a moving direction of the moving constituent, $f_{set}$ denotes a set frequency used for velocity conversion, and $f_d$ denotes the Doppler shift frequency.

23. A diagnostic ultrasound system whereby an object including a moving constituent therein is scanned by an ultrasound beam signal in a contrast echo technique, based on a Doppler technique, in which an ultrasound contrast medium is injected into the object to be placed in the moving constituent, the system comprising:

means for driving an ultrasound probe in order to transmit the ultrasound beam signal toward the object;

means for acquiring an echo signal echoed from the ultrasound contrast medium on the basis of an ultrasound echo signal received by the ultrasound probe;

means for evaluating information of a Doppler shift frequency concerning a nonlinear component of the echo signal on the basis of a reference signal of which frequency is set outside a frequency band of the ultrasound beam signal being transmitted; and means for visualizing the evaluated information of the Doppler shift frequency.

24. A method of ultrasound imaging whereby an object including a moving constituent therein is scanned by an ultrasound beam signal in a contrast echo technique, based on a Doppler technique, in which an ultrasound contrast medium is injected into the object to be placed in the moving constituent, the method comprising the steps of:

driving an ultrasound probe in order to transmit the ultrasound beam signal toward the object;

acquiring an echo signal echoed from the ultrasound contrast medium on the basis of an ultrasound echo signal received by the ultrasound probe;

evaluating information of a Doppler shift frequency concerning a nonlinear component of the echo signal on the basis of a reference signal of which frequency is set outside a frequency band of the ultrasound beam signal being transmitted; and visualizing the evaluated information of the Doppler shift frequency.

* * * * *